(12) United States Patent
Perego et al.

(10) Patent No.: US 6,388,158 B1
(45) Date of Patent: May 14, 2002

(54) PROCESS FOR THE PRODUCTION OF 2,6-DIMETHYLNAPHTHALENE FROM PETROCHEMICAL STREAMS

(75) Inventors: Carlo Perego, Carnate; Giannino Pazzuconi, Broni; Riccardo Mansani, Sassari, all of (IT)

(73) Assignees: Enichem S.p.A., San Donato Milanese; a part interest to each; ENI S.p.A., Rome, both of (IT); a part interest to each ( * ) Notice: Subject to any disclaimer, the term of this patent is extended or adjusted under 35 U.S.C. 154(b) by 0 days.

(21) Appl. No.: 09/604,085

(22) Filed: Jun. 27, 2000

(30) Foreign Application Priority Data

Jul. 13, 1999 (IT) .......................... MI99A1533

(51) Int. Cl.$^7$ .............................................. C07C 15/24
(52) U.S. Cl. ........................ 585/475; 585/470; 585/471
(58) Field of Search ................................ 585/470, 471, 585/475

(56) References Cited

U.S. PATENT DOCUMENTS

| 3,957,896 A | * | 5/1976 | Yokoyama et al. | ......... 260/668 |
| 5,446,226 A | * | 8/1995 | Ozawa et al. | ............... 585/411 |
| 6,147,270 A | * | 11/2000 | Pazzucconi et al. | ........ 585/475 |

FOREIGN PATENT DOCUMENTS

| EP | 0 950 650 | 10/1999 |
| GB | 2 246 788 | 2/1992 |

* cited by examiner

*Primary Examiner*—Walter D. Griffin
(74) *Attorney, Agent, or Firm*—Oblon, Spivak, McClelland, Maier & Neustadt, P.C.

(57) ABSTRACT

Process for the preparation of 2,6-dimethylnaphthalene comprising reacting with at least one aromatic hydrocarbon, in the presence of a zeolitic catalyst, a mixture of naphthalenes comprising a cut obtained by the fractionation of suitable petrochemical streams and subsequent treatment of the product thus obtained with a solid acid.

10 Claims, No Drawings

PROCESS FOR THE PRODUCTION OF 2,6-DIMETHYLNAPHTHALENE FROM PETROCHEMICAL STREAMS

FIELD OF THE INVENTION

The present invention relates to a process for the preparation of 2,6-dimethylnaphthalene comprising reacting a naphthalene substrate with at least one aromatic hydrocarbon in the presence of a zeolitic catalyst, wherein the naphthalene substrate consists of a cut which, obtained by subjecting suitable petrochemical streams to fractionation, is treated with a bed consisting of a solid acid, before being fed to the synthesis of 2,6-dimethylnaphthalene.

2,6-dimethylnaphthalene is an intermediate for the preparation of 2,6-naphthalenedicarboxylic acid, used for obtaining PEN, polyethylenenaphthalene, a polymeric material much better than PET, polyethyleneterephthalate, for various applications.

DESCRIPTION OF THE RELATED ART

Industrial processes for obtaining 2,6-dimethylnaphthalene are based on its recovery from fractions coming from the reforming of kerosene (JP338535—Nippon Mining; U.S. Pat. No. 963,248—Nippon Mining; JP02247136—Nippon Mining; JP02247137—Nippon Mining; JP02304034—Mitsubishi Oil), or from fractions of FCC oil (Chemical Week, Apr. 11, 1992, page 39; Chemical Marketing Reporter, Dec. 10, 1992; European Chemical News, Sep. 28, 1992, page 30; Chemical Week, Jun. 24, 1992, page 27). In the former case, the dimethylnaphthalenes must be separated by distillation and then the 2,6 isomer is isolated by means of selective absorptions and/or crystallizations. In the latter case, there is an additional problem due to the presence of nitrogen and sulfur which poison the catalysts used for the separation and/or isomerization phases.

There is a synthesis process (U.S. Pat. Nos. 4,990,717; 5,118,892; 5,073,670; 5,030,781; 5,012,024), which, by means of alkenylation, cyclization, dehydrogenation, isomerization steps, results in the selective synthesis of 2,6-dimethylnaphthalene, the first step starting from o-xylene and 1,3-butadiene. Alkylation on the part of butadiene on one of the methyl groups of o-xylene, takes place in the presence of a basic catalyst, with the formation of 5-(o-tolyl)2-pentene. The latter is separated and, in the presence of a zeolitic catalyst (Y-type) containing Pt and Cu, is subjected to an internal cyclization reaction. In this way 1,5-dimethyltetraline is formed, which is subsequently dehydrogenated with the help of a Pt/Re catalyst supported on alumina. This is followed by a separation phase to isolate the 1-5-dimethylnaphthalene, which is then isomerized to 2,6 with another zeolitic catalyst.

As can be seen, there are various passages in this synthesis method. This represents a problem from an economic point of view. In addition there are secondary reactions with every passage (chemical reaction) and consequently separations are necessary to guarantee the purity of the intermediates or end-product. The use of a basic catalyst containing Na and K as such or supported, in this particular process, creates handling and safety problems.

The patent U.S. Pat. No. 5,043,501 relates to a synthesis method of 2,6-dimethylnaphthalene in two steps only. The first step comprises the alkylation of an alkylaromatic with a $C_5$ olefin in the presence of a zeolitic catalyst (MCM22). The alkylated product is then dehydrocyclized at 400–500° C. with a catalyst consisting of Pt/Ba/K on L zeolite, obtaining a product containing dimethylnaphthalenes which are then isomerized mainly to 2,6; also in this case there are the problems mentioned above.

Another precursor of 2,6-naphthalenedicarboxylic acid (NDC) is 2,6-di-isopropylnaphthalene. The industrial preparation of this intermediate is described in patents U.S. Pat. Nos. 5,003,120; 5,003,122; 5,026,492. A disadvantage of this process is that the oxidation to carboxylic group of the isopropyl function is more expensive than that of the methyl function.

It is evident, however, that the greatest obstacle in the wide-scale use of PEN lies in the cost of the monomer, 2,6-naphthalene dicarboxylic acid (NDC) (2,6-Naphthalene Dicarboxylic Acid Precursors, May 1993, Chem Systems; High Performance Polyesters, November 1996, Chem Systems; H. P. Muhs, Polyesters Technologies for Fibres & Packaging, De Witt Petrochemical Review, 1997; J. Caldwell, PEN Outlook & Review, De Witt Petrochemical Review, 1998). It is therefore understandable how important it is, regardless of the preparation procedure followed, to be able to intervene in one or more steps of these procedures to obtain a simple and inexpensive selective synthesis of 2,6-dimethylnaphthalene.

The same Applicant, in co-pending Italian patent application MI98A000809 filed on Apr. 17, 1998, described a process for the preparation of 2,6-dimethylnaphthalene starting from naphthalene, methylnaphthalenes, dimethylnaphthalenes, trimethylnaphthalenes and/or polymethylnaphthalenes carried out under at least partially liquid phase conditions and in the presence of suitable aromatic hydrocarbons, catalyzed by a zeolite of the MTW structural type (abbreviation IZA), which allows the selective synthesis of 2,6-dimethylnaphthalene in a single step.

MTW zeolites in particular, when used under the process conditions of this patent application, are more active than the zeolites used according to the conditions described in the known art, especially with respect to BEA and MFI zeolites considered by the known art as being the best catalysts for the preparation of 2,6-dimethylnaphthalene.

BRIEF SUMMARY OF THE INVENTION

The Applicant has now found, and this is an object of the present invention, that it is possible to effect these syntheses, again regardless of the particular procedure followed, using a feeding stream which can be obtained simply and at very competitive costs.

The present invention, in fact, relates to the use, in the synthesis of 2,6-dimethylnaphthalene, of a naphthalene cut obtained by the fractionation of petrochemical streams and the subsequent acid treatment of the product thus obtained.

The present invention relates in particular to a process for the preparation of 2,6-dimethylnaphthalene which comprises reacting, with at least one aromatic hydrocarbon, a mixture of naphthalenes comprising a cut obtained by the fractionation of suitable petrochemical streams and the subsequent treatment of the product thus obtained with a solid acid.

Significant and relatively "clean" quantities of naphthalenes are contained in fractions such as FOK (Fuel Oil Cracking), LCO (Light Cicle Oil) and heavy fractions from catalytic reforming which are not widely exploited at the moment (for example FOK is used as fuel in certain cases). These form an economic source of naphthalenes which can be separated by distillation. For this purpose FOK or LCO petrochemical streams are subjected to fractionation to obtain the specific cut, which contains at least 20% of useful naphthalenes (mainly naphthalene and methylnaphthalenes). During this fractionation, which is carried out using conventional distillation methods, other components are inevitably separated together with the useful naphthalenes. These distill together with the useful naphthalenes because their boiling points fall within the temperature range corresponding to the separation of the cut in question.

Using this cut as naphthalene source for the synthesis of 2,6-dimethylnaphthalene, we have found that, operating according to the object of the present invention, the life of the catalyst can be considerably increased when the feeding to the synthesis of 2,6-dimethylnaphthalene is treated on a pre-bed consisting of solid acid.

DETAILED DESCRIPTION OF THE INVENTION

The present invention therefore relates to an improved process for the preparation of 2,6-dimethylnaphthalene comprising the following steps:

fractionation of a petrochemical stream selected from FOK and LCO;

treatment of the naphthalene cut thus obtained with an acid catalyst;

sending the product thus obtained for reaction with the desired aromatic hydrocarbon in the presence of a catalyst of a zeolitic nature.

Mention has been made of the meaning of the FOK and LCO fractions. As specified, these are subjected to fractionation according to the conventional distillation methods, well known to experts in the field, which can, for example, be effected on a plate column, under vacuum.

The naphthalene cut thus obtained is subjected to treatment with a solid acid, which is effected by sending the cut, before feeding to the synthesis of 2,6-dimethylnaphthalene, onto a pre-bed consisting of said solid acid.

The treatment can take place in batch or in continuous and is carried out at a temperature ranging from room temperature to 360° C., and at a pressure which is such as to guarantee that the operation takes place in liquid phase. The quantity of solid acid varies, with respect to the liquid to be treated, from 0.1% to 5% by weight; the WHSV($h^{-1}$) can vary from 0.1 to 6. Solid acid materials can be used for the purpose, either totally or partially acid, such as clays (montmorillonites, smectites . . . ), or their phyllosilicatic constituents, zeolites, sulfated zirconia, acid resins (for example sulfonic resins), activated and non-activated alumina (optionally chlorinated or fluorinated), acid oxides in general, also in mixtures, amorphous silico-aluminas. Acids and heteropolyacids such as for example $H_3PO_4$ supported on kieselguhr, can also be used.

The reaction of the treated product thus obtained, with the aromatic hydrocarbon for the preparation of 2,6-dimethylnaphthalene or its derivatives, can be effected according to any of the methods known to experts in the field, or, preferably according to the particular process described and claimed in co-pending patent application MI98A 000809 filed on Apr. 17, 1998 by the same Applicant, of which the paragraphs of interest are provided hereunder and form an integrant part of the description of the invention according to the present application.

According to this application, the reaction between the naphthalene hydrocarbon (the above cut pretreated in the case of the process of the present application) and one or more benzene hydrocarbons is carried out, under at least partially liquid phase conditions, in the presence of a zeolite belonging to the MTW structural type and, optionally in the presence of a methylating agent.

Zeolites of the MTW structural type which can be used in the present invention are, for example: ZSM-12, CZH-5, Nu-13, Theta-3 and TPZ-12.

The CZH-5 zeolite is described in GB 2079735A; Nu-1 is described in EP 59059; Theta-3 is described in EP 162719 and TPZ in U.S. Pat. No. 4,557,919.

The MTW structural type zeolite, which is the most suitable for use in the present invention, is a silico-aluminate with a molar ratio $SiO_2/Al_2O_3$ greater than or equal to 20.

This zeolite and its preparation are described in A. Katovic and G. Giordano, Chem. Ind. (Dekker) (Synthesis of Porous Materials) 1997 69, 127–137. The aluminum can be wholly or partly substituted by B, Ga, Fe or their mixtures as described by Toktarev & Jone, in Chon et al., Progress in Zeolites and Microporous Materials, SSSC, vol. 105, 1997.

According to a preferred aspect, ZSM-12 zeolite is used, a porous crystalline material having in its calcined and anhydrous form a molar composition of oxides corresponding to the following formula:

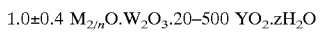

$$1.0 \pm 0.4 \, M_{2/n}O.W_2O_3.20\text{–}500 \, YO_2.zH_2O$$

wherein M is $H^+$ and/or a cation of an alkaline or earth alkaline metal with a valency n, W is selected from aluminum, gallium or their mixtures, Y is selected from silicon and germanium, z ranges from 0 to 60. M is preferably selected from sodium, potassium, hydrogen or their mixtures, W is preferably aluminum and Y is preferably silicon. W can be, at least partially, substituted by boron, iron or their mixtures; the ZSM-12 zeolite is described in U.S. Pat. No. 3,832,449, in Ernst et al., Zeolites, 1987, Vol. 7, September, and in Toktarev & Ione, Chon et al., Progress in Zeolites and Microporous Materials, SSSC, vol. 105, 1997.

A particularly preferred aspect is that the MTW type zeolite used, is in the form in which the cationic sites present in its structure are at least 50% occupied by hydrogen ions. It is especially preferred for 90% of the cationic sites to be occupied by hydrogen ions.

The zeolite can be used as such, pellitized in pure form, or extruded with suitable inorganic binding oxides to form cylindrical, spherical pellets, or having other shapes commonly used, or obtained in the form of microspheres by means of spray-drying, after mixing with a ligand. The ligands may be, for example, aluminas, silicas, silico-aluminas, titania, zirconia or clays. Alumina is preferably used. In the bound catalyst, the zeolite and ligand are in a weight ratio ranging from 10:90 to 90:10, preferably from 25:75 to 75:25.

It is obviously necessary to operate in the presence of the methylating agent when only benzene is used as benzene hydrocarbon together with naphthalene alone as naphthalene substrate.

The feeding of the benzene hydrocarbon is such as to obtain a molar ratio between said hydrocarbon and the naphthalene groups ranging from 1 to 100, more preferably from 3 to 20, wherein naphthalene groups refer to the naphthalene hydrocarbon used as substrate or, when several naphthalene hydrocarbons are present, the sum of their moles.

When the process of the present invention is carried out in the presence of a non-aromatic methylating agent, preferably methanol, a molar ratio between methylating agent and naphthalene groups of less than 30, preferably from 0.1 to 3, is used.

The reaction temperature ranges from 200° C. to 450° C., preferably from 250 to 390° C., even more preferably from 280 to 350° C.; the WHSV space velocity ranges from 0.01 to 8 hours$^{-1}$, preferably from 0.05 to 1 hour$^{-1}$.

It should be noted that the combination between the temperature and pressure conditions should be such as to guarantee that the synthesis of 2,6-dimethylnaphthalene takes place at least partially in liquid phase, and even more preferably substantially in liquid phase.

The pressure used can range from 3 to 60 atm.

The process of the present invention can be industrially carried out in continuous, semi-continuous or batchwise; in order to maintain the temperature within a preferred range, the catalyst can be distributed in various layers in the reactor. A quenching with naphthalene, with the hydrocarbon, or mixture of benzene hydrocarbons used in the process itself, or with the methylating agent, preferably methanol, when present, can be effected between one layer and another.

The temperature control can be obtained, in addition to quenching with reagents and/or inert products, also by inter-cooling between the layers, for example, by the inter-positioning of coolers. The synthesis of 2,6-dimethylnaphthalene can be suitably carried out either in a single reactor in which the catalyst is arranged in two or more beds or in two or more reactors in series, inter-cooled for the temperature control.

When an alkylating agent is used, it can be fed in two or more steps. The alkylating agent is preferably fed in two or more steps along the catalytic beds of the reactor or between these, and/or between the reactors situated in series.

According to a preferred aspect, in order to maximize the production of 2,6-dimethylnaphthalene, the product obtained according to the process of the present invention can be separated into:
(a) a fraction containing benzene hydrocarbons, naphthalene and methylnaphthalene, (b) a fraction containing dimethylnaphthalenes and (c) a fraction containing polymethylated naphthalenes. The desired 2,6-dimethylnaphthalene isomer is isolated from fraction (b) of dimethylnaphthalenes, whereas the remaining fraction (d), containing dimethylnaphthalenes different from the 2,6 isomer, and fractions (a) and (c), are re-fed to the initial reactor where they re-enter the reactive cycle. Alternatively, said fraction (d) and fractions (a) and (c), optionally enriched with naphthalene and/or methylnaphthalene, can be fed to a specific reactor where they are reacted, under at least partially liquid phase conditions, in the presence of a zeolite belonging to the MTW structural type, with one or more benzene hydrocarbons selected from benzene, toluene, xylenes, trimethylbenzenes, tetramethylbenzenes, pentamethylbenzene and/or hexamethylbenzene. The reaction temperature ranges from 200 to 450° C., and the space velocity ranges from 0.01 to 8 hrs$^{-1}$.

According to another aspect of the present invention, in order to maximize the production of 2,6-methylnaphthalene, fraction (d) containing dimethylnaphthalenes different from 2,6-dimethylnaphthalene, in particular 1,6 and 1,5 isomer, is subjected to isomerization, under at least partially liquid phase conditions, in the presence of a catalyst containing an MTW zeolite, at a temperature ranging from 100 to 400° C., more preferably from 120 to 250° C., even more preferably from 130 to 200° C.

This particular isomerization process of 1,6-dimethylnaphthalene and 1,5-dimethylnaphthalene, pure or mixed with other isomers of dimethylnaphthalene, to give 2,6-dimethylnaphthalene, catalyzed by a zeolite of the MTW type, is in itself new and is a further object of the present invention.

The exhausted catalyst deriving from the process for preparing 2,6-dimethylnaphthalene can be regenerated by means of the known combustion methods of coke or its precursors which typically account for the deactivation of the solid acid materials which catalyze reactions in which hydrocarbons are involved. We have now unexpectedly found a method for regenerating this exhausted catalyst in a much simpler and more economic way.

With respect to the traditional regenerative methods, this new method does not require either the removal of the catalyst from the reaction environment or the high temperatures necessary for the combustion of coke. A further aspect of the present invention therefore relates to a method for regenerating the exhausted catalyst deriving from the preparation process of 2,6-dimethylnaphthalene by the reaction of a naphthalene hydrocarbon selected from naphthalene, methylnaphthalenes, dimethylnaphthalenes, trimethylnaphthalenes, tetramethylnaphthalenes, pentamethylnaphthalenes, hexamethylnaphthalene or their mixtures with one or more benzene hydrocarbons selected from benzene, toluene, xylenes, trimethylbenzenes, tetramethylbenzenes, pentamethylbenzene and/or hexamethylbenzene, under at least partially liquid phase conditions, in the presence of a zeolite belonging to the MTW structural type and optionally in the presence of a methylating agent, wherein said regeneration method comprises treating the exhausted catalyst with one or more of said benzene hydrocarbons, at a temperature ranging from 200° to 450° C., more preferably from 250° to 400° C., even more preferably from 280° to 370° C., said temperature being at least equal to that used during the preparation process of 2,6-dimethylnaphthalene from which the exhausted catalyst derives. The regeneration conditions are selected so as to operate in at least partially liquid phase, the WHSV space velocity can range from 0.01 to 8 hours$^{-1}$ and the pressure can be selected from 5 to 60 atm.

Further details can be obtained on reading the following operating examples which provide a better illustration of the invention without limiting its scope.

EXAMPLE 1

Preparation of the Active Phase of the Catalyst 2.4 grams of sodium aluminate at 56% of $Al_2O_3$ are dissolved in 84 grams of aqueous solution of tetraethylammonium hydroxide at 35%. The limpid solution thus obtained is poured, under stirring, into 200 grams of Ludox HS 40 colloidal silica. After brief stirring, a limpid, homogeneous gel is obtained which is poured into an AISI316 steel autoclave, equipped with an anchor stirrer. The gel is left to crystallize under hydrothermal conditions at 160° C. for about 70 hours.

At this point the autoclave is cooled and the solid separated from the mother liquor and washed with demineralized water until the washing water has a pH of less than 9.

The solid is calcined at 550° C. in an atmosphere of air for 5 hours. It is then suspended in a solution of demineralized water and ammonium acetate, the latter in an excess molar quantity, for example 5 times, with respect to the aluminum formally present from synthesis. During this operation the sodium present from synthesis in the zeolite is substituted by the ammonium ion, as a result of ion exchange. This first exchange is followed by a washing, a second exchange with the same procedure as the first and another washing. The solid is then definitively separated from the aqueous environment, dried and calcined for 5 hours at 550° C. in an atmosphere of air. In this way the zeolitic catalyst is obtained in acid form.

An XRD analysis is carried out on the end sample, which shows the presence of a sole MTW-type zeolitic crystalline phase, together with a chemical analysis on the basis of which the residual sodium content proves to be less than 50 ppm and the molar ratio $SiO_2/Al_2O_3$ is 99.

The zeolite in acid form thus obtained can be formed as pellets by means of extrusion with a suitable ligand, such as alumina, or other ligands available in the known art.

EXAMPLE 2 (INVENTIVE)
Test with Pretreatment of the Charge with a Solid Acid A fraction containing 75.1% (weight) of naphthalene and methylnaphthalenes; a few (less than 1%) dimethylnaphthalenes, is distilled from a sampling of FOK from the steam cracking (pyrolysis) of virgin naphtha. The remaining 24.9% consists of a range of various chemical species (about 40 identified). Among these the most significant are: indene, dihydronaphthalene, 1-methylindene, 3-methylindene, 2,3-dimethyldihydroindene, 1,2-dihydromethylnaphthalene.

The FOK distillate is diluted in trimethylbenzene so that the end molar ratio between the trimethylbenzene and the sum of the moles of naphthalene, monomethylnaphthalenes, dimethylnaphthalenes, is equal to ten.

In this example, this mixture, before being fed to the reactor for the acid catalyzed synthesis of 2,6-dimethylnaphthalene, is pretreated with a solid acid. In this case the pretreatment is carried out with an acid montmorillonite (clay). The pretreatment can take place either in continuous or batch and the solid can be used as such or dehydrated before use, for example at 200° C. in a stream of dry nitrogen or air. The montmorillonite was used, in the present example, in a ratio of 3% by weight with respect to the quantity of liquid, at a temperature of 80° C. approx. in batch for 5 hours.

On comparing the gaschromatographic analysis of the mixture before and after the pretreatment, it can be observed that:
- the naphthalene, methylnaphthalenes, dimethylnaphthalenes do not undergo quantitative variations, within the error limits of the analysis method, following the action of the solid acid;
- the non-naphthalene components of FOK, such as those already mentioned, after pretreatment can no longer be detected or their quantity however is considerably reduced (at least 50%).

In any case, after pretreatment, it is also possible to add a certain quantity of methanol to the feeding for the reactor, in order to stoichiometrically supply the methyl groups necessary for the alkylation of the naphthalenes. In this way it is possible not to deprive the solvent of methyls, so that it can be recycled after separation of the desired product. The naphthalene, methylnaphthalenes, dimethylnaphthalenes (isomers different from 2,6) and in general polymethylnaphthalenes, can also be recycled.

The catalytic test is carried out as follows. Four grams of zeolite of the MTW structural type (such as for example ZSM12 obtained according to example 1) in the form of tablets and granulated within the range of 20–40 mesh, are charged into the isothermal zone of a fixed-bed reactor, with quartz above and below as inert filling. The temperature of the reactor is brought to 200° C. for at least two hours, under a stream of nitrogen against atmospheric pressure. The reactor, maintained under a stream of inert gas, is cooled to room temperature and the reagents, prepared as described above, are then fed until the reactor has been pressurized to 40 bar.

At this stage the reactor is heated and the temperature is brought to 350° C. This test is therefore carried out under liquid phase conditions with respect to the state of the reagents and products. The WHSV ($h^{-1}$) (with respect to the total mixture) is 2. The products leaving the reactor are cooled and analyzed by means of gaschromatography. Samplings of the products are taken at regular time intervals (time on stream).

After 51 hours of reaction, the mixture of products, solvent-free, has the following composition, expressed in weight % (the data relating to the feeding are indicated between brackets):

naphthalene: 9.3 (45.4)
1-methylnaphthalene: 9.4 (20.4)
2-methylnaphthalene: 21.4 (32.6)
2,6-dimethylnaphthalene: 15.5 (0.0)
2,7-dimethylnaphthalene: 6.5 (1.6)
1,3-1,7-dimethylnaphthalene: 7.8 (0.0)
1,6-dimethylnaphthalene: 13.8 (0.0)
1,4-2,3-dimethylnaphthalene: 1.1 (0.0)
1,5-dimethylnaphthalene: 2.3 (0.0)
1,2-dimethylnaphthalene: 0.8 (0.0)
1,8-dimethylnaphthalene: 0.0 (0.0)
trimethylnaphthalenes (various isomers): 12.1 (0.0)

After 148 hours of reaction, the mixture of products, solvent-free, has the following composition, expressed in weight % (the data relating to the feeding are indicated between brackets):

naphthalene: 12.1 (45.4)
1-methylnaphthalene: 10.5 (20.4)
2-methylnaphthalene: 23.9 (32.6)
2,6-dimethylnaphthalene: 14.4 (0.0)
2,7-dimethylnaphthalene: 6.1 (1.6)
1,3-1,7-dimethylnaphthalene: 7.0 (0.0)
1,6-dimethylnaphthalene: 13.0 (0.0)
1,4-2,3-dimethylnaphthalene: 1.1 (0.0)
1,5-dimethylnaphthalene: 2.2 (0.0)
1,2-dimethylnaphthalene: 0.8 (0.0)
1,8-dimethylnaphthalene: 0.0 (0.0)
trimethylnaphthalenes (various isomers): 8.9 (0.0)

EXAMPLE 3 (COMPARATIVE)
Test without any Type of Pretreatment

A fraction containing 75.1% (weight) of naphthalene and methylnaphthalenes; a few (less than 1%) dimethylnaphthalenes, is distilled from a sampling of FOK from the steam cracking of virgin naphtha. The remaining 24.9% consists of a range of various chemical species (about 40 identified). Among these the most significant are: indene, dihydronaphthalene, 1-methylindene, 3-methylindene, 2,3-dimethyldihydroindene, 1,2-dihydromethylnaphthalene.

The FOK distillate is diluted in trimethylbenzene so that the end molar ratio between the trimethylbenzene and the sum of the moles of naphthalene, monomethylnaphthalenes, dimethylnaphthalenes, is equal to ten. In this example, this mixture is used as such, as feeding. In any case it is also possible to add a certain quantity of methanol for the purpose of stoichiometrically supplying the methyl groups necessary for the alkylation of the naphthalenes. In this way it is possible not to deprive the solvent of methyls, so that it can be recycled after separation of the desired product. The naphthalene, methylnaphthalenes, dimethylnaphthalenes (isomers different from 2,6) and generally polymethylnaphthalenes, can also be recycled.

The catalytic test is carried out as follows. Four grams of zeolite of the MTW structural type (such as for example ZSM12 obtained according to example 1) in the form of tablets and granulated within the range of 20–40 mesh, are charged into the isothermal zone of a fixed-bed reactor, with quartz above and below as inert filling. The temperature of the reactor is brought to 200° C. for at least two hours, under a stream of nitrogen against atmospheric pressure. The reactor, maintained under a stream of inert gas, is cooled to room temperature and the reagents, prepared as described above, are then fed until the reactor has been pressurized to 40 bar.

At this stage the reactor is heated and the temperature is brought to 350° C. This test is therefore carried out under liquid phase conditions, with respect to the state of the reagents and products. The WHSV ($h^{-1}$) (with respect to the total mixture) is 2. The products leaving the reactor are cooled and analyzed by means of gaschromatography. Samplings of the products are taken at regular time intervals (time on stream).

After 51 hours of reaction, the mixture of products, solvent-free, has the following composition, expressed in weight % (the data relating to the feeding are indicated between brackets):

naphthalene: 10.4 (45.4)
1-methylnaphthalene: 9.9 (20.4)
2-methylnaphthalene: 22.4 (32.6)
2,6-dimethylnaphthalene: 14.9 (0.0)
2,7-dimethylnaphthalene: 6.6 (1.6)
1,3-1,7-dimethylnaphthalene: 7.4 (0.0)
1,6-dimethylnaphthalene: 13.5 (0.0)
1,4-2,3-dimethylnaphthalene: 1.1 (0.0)
1,5-dimethylnaphthalene: 2.3 (0.0)
1,2-dimethylnaphthalene: 0.8 (0.0)
1,8-dimethylnaphthalene: 0.0 (0.0)
trimethylnaphthalenes (various isomers): 10.6 (0.0)

After 148 hours of reaction, the mixture of products, solvent-free, has the following composition, expressed in weight % (the data relating to the feeding are indicated between brackets):

naphthalene: 32.8 (45.4)
1-methylnaphthalene: 16.8 (20.4)
2-methylnaphthalene: 29.7 (32.6)
2,6-dimethylnaphthalene: 5.5 (0.0)
2,7-dimethylnaphthalene: 2.5 (1.6)
1,3-1,7-dimethylnaphthalene: 2.7 (0.0)
1,6-dimethylnaphthalene: 5.1 (0.0)
1,4-2,3-dimethylnaphthalene: 0.4 (0.0)
1,5-dimethylnaphthalene: 0.8 (0.0)
1,2-dimethylnaphthalene: 0.3 (0.0)
1,8-dimethylnaphthalene: 0.0 (0.0)
trimethylnaphthalenes (various isomers): 3.4 (0.0)

From examples 3 and 4 it can be observed that pretreatment of the charge with acid montmorillonite causes a considerable improvement in the life of the catalyst. In fact, when the charge has undergone pretreatment, the production of dimethylnaphthalenes, and 2,6 isomer, remains at values very similar to the initial values, even after about 150 hours of reaction; in the other case a significant decrease in the formation of dimethylnaphthalenes, and 2,6 isomer, is noted.

EXAMPLE 4 (COMPARATIVE)

Test with Pre-hydrogenation

A fraction containing 75.1% (weight) of naphthalene and methylnaphthalenes; a few (less than 1%) dimethylnaphthalenes, is distilled from a sampling of FOK from the steam cracking of virgin naphtha. The remaining 24.9% consists of a range of various chemical species (about 40 identified). Among these the most significant are: indene, dihydronaphthalene, 1-methylindene, 3-methylindene, 2,3-dimethyldihydroindene, 1,2-dihydromethylnaphthalene.

The FOK distillate is diluted in trimethylbenzene so that the end molar ratio between the trimethylbenzene and the sum of the moles of naphthalene, monomethylnaphthalenes, dimethylnaphthalenes, is equal to ten.

In this case the mixture, before being used as feeding for the same purposes as example 2, i.e. the acid-catalyzed synthesis of 2,6-dimethylnaphthalene, is subjected to hydrogenation. This operation is carried out in an autoclave at 170° C., with a Pt catalyst on carbon at 50 bar of hydrogen, for 5 hours. Following the hydrogenation, gaschromatographic analysis of the liquid used as feeding shows the disappearance of the signals relating to the species containing bonds of the olefinic type and the appearance of the corresponding hydrogenated species. Under the conditions and with the catalyst specified above, there is no hydrogenation of aromatic chemical species (benzene and naphthalene).

In any case after hydrogenation, it is also possible to add a certain quantity of methanol for the purpose of stoichiometrically supplying the methyl groups necessary for the alkylation of the naphthalenes. In this way it is possible not to deprive the solvent of methyls, so that it can be recycled after separation of the desired product. The naphthalene, methylnaphthalenes, dimethylnaphthalenes (isomers different from 2,6) and in general polymethylnaphthalenes, can also be recycled.

The catalytic test is carried out as follows. Four grams of zeolite of the MTW structural type (such as for example ZSM12 obtained according to example 1) in the form of tablets and granulated within the range of 20–40 mesh, are charged into the isothermal zone of a fixed-bed reactor, with quartz above and below as inert filling. The temperature of the reactor is brought to 200° C. for at least two hours, under a stream of nitrogen against atmospheric pressure. The reactor, maintained under a stream of inert gas, is cooled to room temperature and the reagents, prepared as described above, are then fed until the reactor has been pressurized to 40 bar.

At this stage the reactor is heated and the temperature is brought to 350° C. This test is therefore carried out under liquid phase conditions with respect to the state of the reagents and products. The WHSV ($h^{-1}$) (with respect to the total mixture) is 2. The products leaving the reactor are cooled and analyzed by means of gaschromatography. Samplings of the products are taken at regular time intervals (time on stream).

After 51 hours of reaction, the mixture of products, solvent-free, has the following composition, expressed in weight % (the data relating to the feeding are indicated between brackets):

naphthalene: 10.0 (45.4)
1-methylnaphthalene: 9.6 (20.4)
2-methylnaphthalene: 22.1 (32.6)
2,6-dimethylnaphthalene: 15.1 (0.0)
2,7-dimethylnaphthalene: 6.6 (1.6)
1,3-1,7-dimethylnaphthalene: 7.5 (0.0)
1,6-dimethylnaphthalene: 13.6 (0.0)
1,4-2,3-dimethylnaphthalene: 1.1 (0.0)
1,5-dimethylnaphthalene: 2.2 (0.0)
1,2-dimethylnaphthalene: 0.9 (0.0)

1,8-dimethylnaphthalene: 0.0 (0.0)

trimethylnaphthalenes (various isomers): 11.3 (0.0)

After 148 hours of reaction, the mixture of products, solvent-free, has the following composition, expressed in weight % (the data relating to the feeding are indicated between brackets):

naphthalene: 31.7 (45.4)

1-methylnaphthalene: 16.1 (20.4)

2-methylnaphthalene: 28.8 (32.6)

2,6-dimethylnaphthalene: 6.1 (0.0)

2,7-dimethylnaphthalene: 2.8 (1.6)

1,3-1,7-dimethylnaphthalene: 3.1 (0.0)

1,6-dimethylnaphthalene: 5.6 (0.0)

1,4-2,3-dimethylnaphthalene: 0.6 (0.0)

1,5-dimethylnaphthalene: 1.1 (0.0)

1,2-dimethylnaphthalene: 0.4 (0.0)

1,8-dimethylnaphthalene: 0.0 (0.0)

trimethylnaphthalenes (various isomers): 3.7 (0.0)

What is claimed is:

1. A process for the preparation of 2,6-dimethylnaphthalene comprising reacting in a synthesis reaction with at least one aromatic hydrocarbon, in the presence of a zeolitic catalyst, a mixture of naphthalenes comprising a cut obtained by the fractionation of a petrochemical stream comprising a mixture of naphthalenes and the subsequent pretreatment of the cut thus obtained with a solid acid by contacting the cut with the solid acid before being fed to the synthesis reaction.

2. The process for the preparation of 2,6-dimethylnaphthalene according to claim 1, wherein the treatment of the cut of the petrochemical stream is carried out by sending the cut onto a bed consisting of a solid acid.

3. The process for the preparation of 2,6-dimethylnaphthalene according to claim 1 or 2, wherein the solid acid is selected from clays, montmorillonites, smectites, or their phyllosilicatic constituents in acid form, natural or synthetic zeolites in at least partially acid form, sulfated oxides, activated or non-activated aluminas, optionally chlorinated or fluorinated, mixed acid oxides, amorphous silico-aluminas, supported acids and heteropolyacids, or acid resins.

4. The process for the preparation of 2,6-dimethylnaphthalene according to claim 1 or 2, wherein the treatment of the cut of the petrochemical stream is carried out at a temperature ranging from room temperature to 360° C.

5. The process for the preparation of 2,6-dimethylnaphthalene according to claim 1 or 2, wherein the treatment of the cut of the petrochemical stream is carried out at a pressure which is such as to guarantee that the operation takes place in liquid phase.

6. The process for the preparation of 2,6-dimethylnaphthalene according to claim 1, wherein the cut to be subjected to treatment is obtained by the fractionation of FOK, LCO, or the fraction of heavy products from catalytic reforming.

7. The process according to claim 6, wherein the treatment of the cut of the petrochemical stream is carried out at a temperature ranging from room temperature to 360° C.

8. The process according to claim 1, wherein the solid acid is a zeolite.

9. The process according to claim 1, wherein the solid acid is montmorillonite.

10. The process according to claim 1, wherein the zeolitic catalyst has the MTW structure.

\* \* \* \* \*